US009945701B2

(12) United States Patent
Jelken et al.

(10) Patent No.: US 9,945,701 B2
(45) Date of Patent: Apr. 17, 2018

(54) ACTUATOR BRACKET HAVING A SENSOR

(71) Applicant: Fisher Controls International LLC, Marshalltown, IA (US)

(72) Inventors: Shannon Eugene Jelken, Marshalltown, IA (US); Mark Allen Rachuy, Marshalltown, IA (US); Benjamin Uriah Good, Marshalltown, IA (US)

(73) Assignee: FISHER CONTROLS INTERNATIONAL LLC, Marshalltown, IA (US)

( * ) Notice: Subject to any disclaimer, the term of this patent is extended or adjusted under 35 U.S.C. 154(b) by 58 days.

(21) Appl. No.: 14/802,209

(22) Filed: Jul. 17, 2015

(65) Prior Publication Data

US 2017/0016749 A1 Jan. 19, 2017

(51) Int. Cl.

*G01D 11/30* (2006.01)
*G01P 15/00* (2006.01)
*G01N 29/14* (2006.01)
*G01L 1/00* (2006.01)
*G01L 1/22* (2006.01)
*F16K 37/00* (2006.01)

(52) U.S. Cl.

CPC .......... *G01D 11/30* (2013.01); *F16K 37/0041* (2013.01); *G01L 1/00* (2013.01); *G01L 1/22* (2013.01); *G01N 29/14* (2013.01); *G01P 15/00* (2013.01)

(58) Field of Classification Search

CPC ...... G01D 11/30; F16K 37/0041; F16M 1/00; F16M 13/00; F16M 13/005; F16M 2200/00

See application file for complete search history.

(56) References Cited

U.S. PATENT DOCUMENTS 2,603,983 A 7/1952 Rieser
3,326,503 A 6/1967 Bade
3,395,594 A 8/1968 Blair
3,516,627 A 6/1970 Gable et al.

(Continued)

FOREIGN PATENT DOCUMENTS

CN 201176491 1/2009
DE 202007004176 6/2007

(Continued)

OTHER PUBLICATIONS

International Searching Authority, "International Search Report and Written Opinion", issued in connection with International Application No. PCT/US2016/042735, dated Nov. 29, 2016 (13 pages).

*Primary Examiner* — Lisa Caputo
*Assistant Examiner* — Philip Cotey
(74) *Attorney, Agent, or Firm* — Hanley, Flight & Zimmerman, LLC

(57) ABSTRACT

Actuator bracket having a sensor is disclosed. An example apparatus includes a bracket having a first side and a second side opposite the first side. The first side is to couple to a first surface of an actuator. The second side is to couple to a controller. The apparatus also includes a first sensor coupled to the first side of the bracket. When the bracket is coupled to the first surface of the actuator, the first sensor is adjacent the first surface to measure a characteristic of the first surface of the actuator.

20 Claims, 7 Drawing Sheets

(56) References Cited

U.S. PATENT DOCUMENTS

| | | | | |
|---|---|---|---|---|
| 4,033,531 | A | 7/1977 | Levine | |
| 4,719,939 | A | 1/1988 | Killian | |
| 4,849,667 | A | 7/1989 | Morrill | |
| 4,879,901 | A | 11/1989 | Leon | |
| 5,160,113 | A | 11/1992 | Whiddon | |
| 5,743,133 | A | 4/1998 | Watanabe | |
| 6,137,204 | A * | 10/2000 | Kuwahara | H02K 24/00 310/162 |
| 6,304,016 | B1 | 10/2001 | Frederick et al. | |
| 6,450,782 | B1 | 9/2002 | Sakamoto | |
| 7,360,313 | B1 | 4/2008 | Hamm et al. | |
| 7,510,163 | B2 | 3/2009 | Schlitzkus et al. | |
| 7,641,172 | B2 | 1/2010 | Richards et al. | |
| 3,004,135 | A1 | 8/2011 | Peterson et al. | |
| 8,004,135 | B2 * | 8/2011 | Peterson | H02K 11/33 310/156.05 |
| 8,342,478 | B1 | 1/2013 | Cordray et al. | |
| 9,097,269 | B2 * | 8/2015 | Rachuy | F04B 39/0044 |
| 2002/0090258 | A1 | 7/2002 | Lewis et al. | |
| 2004/0154466 | A1 * | 8/2004 | Gethmann | F16K 37/0008 92/5 R |
| 2006/0071131 | A1 | 4/2006 | Young et al. | |
| 2007/0034264 | A1 * | 2/2007 | Kunz | F16K 37/0041 137/554 |
| 2007/0132423 | A1 * | 6/2007 | Ajima | H02P 6/10 318/719 |
| 2007/0227295 | A1 | 10/2007 | Leimann | |
| 2008/0142674 | A1 | 6/2008 | Dang et al. | |
| 2008/0174213 | A1 * | 7/2008 | Peterson | H02K 11/33 310/68 R |
| 2010/0123057 | A1 * | 5/2010 | Song | F16M 11/2021 248/188.2 |
| 2011/0017477 | A1 * | 1/2011 | Combs | A62C 35/68 169/16 |
| 2011/0021930 | A1 * | 1/2011 | Mazzeo | A61B 5/0002 600/485 |
| 2011/0094160 | A1 * | 4/2011 | Houser | E05F 15/63 49/31 |
| 2011/0164870 | A1 * | 7/2011 | Manson | F16M 11/14 396/428 |
| 2011/0183805 | A1 * | 7/2011 | Chan | B62M 6/50 475/254 |
| 2012/0007457 | A1 | 1/2012 | Andersson et al. | |
| 2013/0299269 | A1 * | 11/2013 | Tsunoda | B62D 5/0406 180/444 |
| 2013/0320184 | A1 * | 12/2013 | Rachuy | F04B 39/0044 248/638 |
| 2013/0327403 | A1 | 12/2013 | Jensen | |
| 2014/0005960 | A1 | 1/2014 | Anderson et al. | |
| 2015/0047720 | A1 * | 2/2015 | Tamba | F16K 37/0041 137/468 |

FOREIGN PATENT DOCUMENTS

| | | |
|---|---|---|
| JP | 5745256 | 3/1982 |
| JP | 2007209185 | 8/2007 |

* cited by examiner

ACTUATOR BRACKET HAVING A SENSOR

FIELD OF THE DISCLOSURE

This patent relates generally to actuator brackets and, more particularly, to an actuator bracket having a sensor.

BACKGROUND

Actuators are commonly used to operate devices such as flow control members in valves. A controller may be used to measure characteristics of an actuator and control a position of a stem of the actuator. In some instances, the controller is coupled to the actuator to enable the controller to control the actuator.

SUMMARY

In one example, an apparatus includes a bracket having a first side and a second side opposite the first side. The first side is to couple to a first surface of an actuator. The second side is to couple to a controller. The apparatus also includes a first sensor coupled to the first side of the bracket. When the bracket is coupled to the first surface of the actuator, the first sensor is adjacent the first surface to measure a characteristic of the first surface of the actuator.

In another example, an apparatus includes a bracket to couple a controller to an actuator. The bracket has a first end, a second end opposite the first end, and a first side extending from the first end to the second end. The first end is to couple to an actuator and the second end is to couple to a controller. The apparatus also includes a first sensor coupled to the first side at the first end of the bracket. The first sensor is to measure a characteristic of the first end when the bracket is coupled to the actuator.

In another example, an apparatus includes means for coupling a controller to a surface of an actuator and means for sensing a characteristic coupled to the means for coupling. When the means for coupling is coupled to the actuator, the means for sensing is adjacent the surface to measure a characteristic of the means for coupling.

BRIEF DESCRIPTION OF THE DRAWINGS

The figures are not to scale. Instead, to clarify multiple layers and regions, the thicknesses of the layers may be enlarged in the drawings. Wherever possible, the same reference numbers will be used throughout the drawing(s) and accompanying written description to refer to the same or like parts.

DETAILED DESCRIPTION

Figure 1:
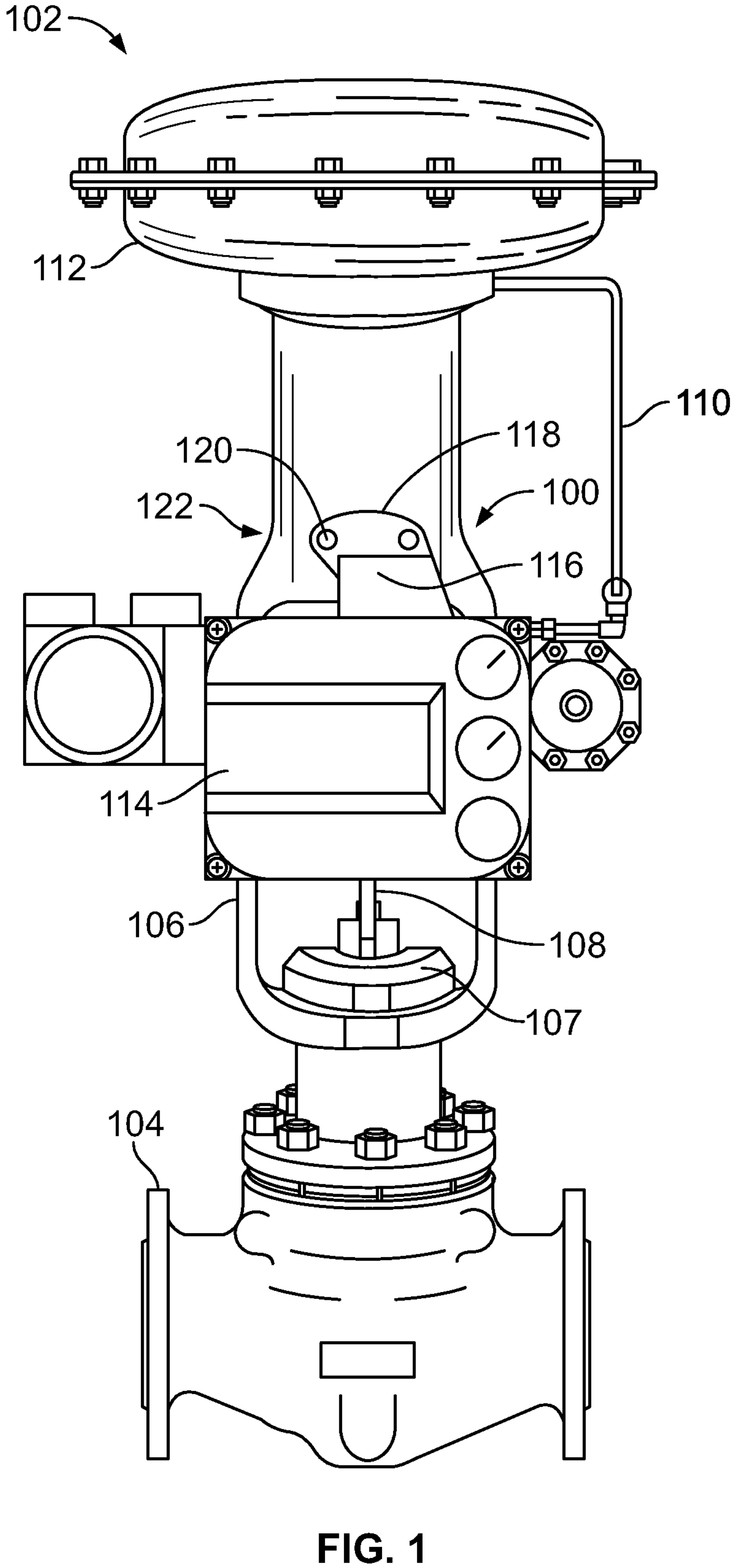
FIG. 1 depicts an example bracket assembly for coupling a controller to an actuator in accordance with the teachings herein.

Controllers may be used to control actuators that operate valves. For example, some known controllers may be used to control a position of an actuator stem that is operatively coupled to a flow control member of a valve by providing control fluid to the actuator. To enable the controller to accurately provide the control fluid to the actuator, some known controllers are coupled to a yoke of the actuator via a bracket. In some instances, repeated movement and/or vibration of the actuator may loosen the bracket from the actuator and/or the controller over time. A loose coupling between the bracket and the actuator and/or between the bracket and the controller may result in imprecise control of the actuator and/or structural damage to the actuator, the bracket and/or the controller. For example, if the bracket remains loosely coupled to the actuator for an extended period of time, continued vibration and/or movement of the actuator may result in the bracket and the controller decoupling from the actuator. Additionally or alternatively, repeated movement and/or vibration of the actuator may damage other components of the actuator. In some examples, vibrations of the actuator may cause cracking of the yoke, loosening of a yoke lock nut and/or failure of supply line tubing between the controller and the actuator.

The example bracket disclosed herein includes a sensor to measure a characteristic of an actuator and/or a bracket coupling a controller to the actuator. For example, the sensor measures a characteristic of the bracket or the actuator that is indicative of a degree to which the bracket is securely and/or rigidly coupled to the actuator. To accurately measure the characteristic of the coupling, the sensor is positioned immediately adjacent to where the bracket couples to the actuator. Further, the characteristic measured by the sensor is indicative of a characteristic of an actuator yoke, a yoke lock nut, actuator supply line tubing and/or a coupling of the bracket and a controller. In some examples, the bracket includes a second sensor. A comparison of characteristics measured by the sensors further enables identification of a characteristic of the actuator yoke, the yoke lock nut, the actuator supply line tubing, the coupling of the bracket and the controller and/or the coupling of the bracket and the actuator. Thus, the example bracket monitors the bracket and/or the actuator to detect failure and/or degradation of the actuator, the bracket, the coupling between the bracket and the actuator and/or the coupling between the controller and the actuator.

An example bracket assembly disclosed herein includes a bracket having a first side that is to couple to a first surface of an actuator and a second side that is to couple to a controller. A first sensor (e.g., a force gauge, a strain gauge, an accelerometer, an acoustic emission sensor) of the example bracket assembly is coupled to the first side of the bracket. When the bracket of the example bracket assembly is coupled to the first surface of the actuator, the first sensor is adjacent the first surface to measure a characteristic (e.g., stress, strain, acceleration of vibrations, acoustic emissions) of a coupling of the actuator. For example, by measuring acceleration of vibrations of a portion of the bracket that is adjacent the coupling, the first sensor identifies if the bracket is loosened and/or decoupled from the actuator.

In some examples, the first sensor of the example bracket assembly is coupled to the bracket between ribs defined by the first side of the bracket and recessed from an outer edge of the ribs to protect the first sensor from being damaged. At least one of the ribs has an outer edge that defines a groove to receive a wire coupled to the first sensor. The groove prevents the wire from being pinched, severed and/or otherwise damaged when the bracket is coupled to the actuator. Thus, the example bracket apparatus substantially reduces the risk of the sensor being damaged or dislodged.

In some examples, the bracket has a first end that is to couple to the actuator and a second end opposite the first end that is to couple to the controller. The first sensor is coupled at the first end of the bracket and a second sensor is coupled at the second end of the bracket. The second sensor measures a characteristic of the second end when the controller is coupled to the bracket. In such examples, the characteristics measured by the first sensor and the second sensor are compared to determine if the controller is loosened and/or decoupled from the bracket.

In some examples, the bracket assembly includes another sensor that is to couple to a second surface of the actuator different than the first surface. The other sensor measures a characteristic of the second surface of the actuator. In some examples, the first sensor and the other sensor are communicatively coupled to the controller to enable the characteristic of the coupling and the second surface of the actuator to be compared. For example, by comparing the characteristics of the coupling and the second surface of the actuator, the controller can determine if an actuator component adjacent the second surface of the actuator (e.g., a component of an actuator casing, a diaphragm plate) is loosened and/or decoupled.

FIG. 1 illustrates an example bracket assembly 100 in accordance with the teachings herein. An actuator 102 of the illustrated example controls fluid flow through a fluid valve 104. For example, the actuator 102 includes a yoke 106, a yoke lock nut 107, a stem 108, tubing 110, and an actuator casing 112. The yoke 106 couples the actuator casing 112 and the fluid valve 104. The tubing 110 operatively couples a controller 114 (e.g., a positioner) to a pressure chamber defined by the actuator casing 112. The stem 108 operatively couples a diaphragm within the pressure chamber and a valve plug of the fluid valve 104.

In operation, the controller 114 measures a current position of the stem 108. Based on the current position and a desired position of the stem 108, the controller 114 provides control fluid (e.g., pressurized air) to the pressure chamber via the tubing 110 to change a pressure within the pressure chamber. The change in pressure causes the diaphragm and, thus, the stem 108 of the actuator 102 to move. In turn, the stem 108 causes the valve plug to move relative to a valve seat of the fluid valve 104 to increase and/or decrease fluid flow through the fluid valve 104. Thus, the controller 114 of the illustrated example controls the fluid flow through the fluid valve 104.

In the illustrated example, the controller 114 is coupled to the yoke 106 to enable the controller 114 to precisely control the actuator 102. For example, coupling the controller 114 to the actuator 102 enables the controller 114 to accurately measure the position of the stem 108 and/or reduce the distance that the control fluid travels between the controller 114 and the pressure chamber. As illustrated in FIG. 1, the controller 114 is coupled to the actuator 102 via a bracket 116 of the example bracket assembly 100. A first end 118 of the bracket 116 is coupled to the yoke 106 via fasteners 120 to form a coupling 122 of the bracket 116 and the actuator 102. The controller 114 of the illustrated example couples to a second end (e.g., a second end 202 of FIG. 2) of the bracket 116 opposite the first end 118. In some examples, the second end 202 of the bracket 116 is unsupported by or free from the actuator 102. In other words, the bracket assembly 100 forms a cantilever in which the first end 118 is fixed to the yoke 106 and the second end 202 is an unsupported end.

Figure 2:
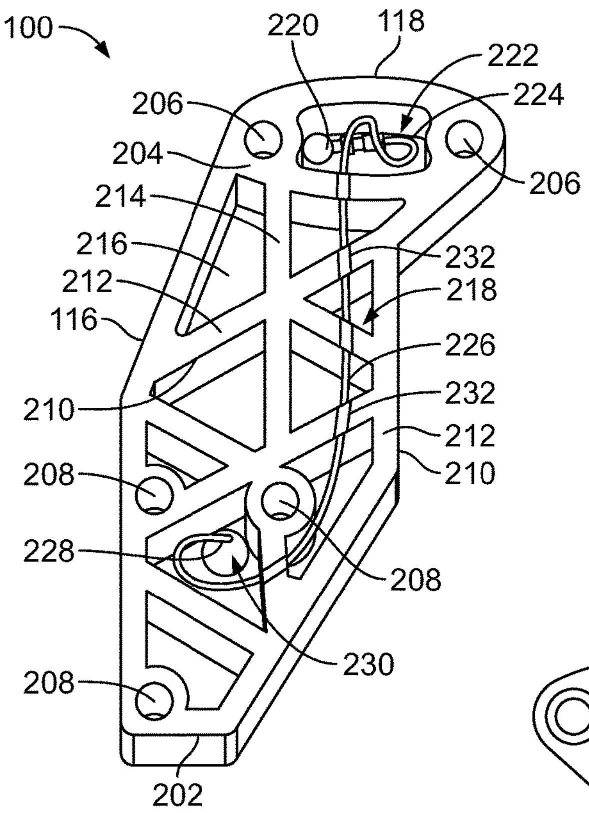
FIG. 2 depicts a first side of a bracket of the bracket assembly of FIG. 1.

FIG. 2 depicts a first side 204 of the bracket 116. As illustrated in FIG. 2, the bracket 116 includes the first end 118 and the second end 202 opposite the first end 118. The first end 118 of the bracket 116 defines apertures 206, and the second end 202 of the bracket 116 defines apertures 208. The apertures 206, 208 of the bracket 116 extend between the first side 204 and an opposing second side (e.g., a second side 302 of FIG. 3) of the bracket 116.

In the illustrated example, the first side 204 at the first end 118 of the bracket 116 is to couple to a surface of the yoke 106 (FIG. 1) to securely fix, couple and/or fasten the bracket 116 to the actuator 102 (FIG. 1). To couple the bracket 116 to the actuator 102, the apertures 206 at the first end 118 of the illustrated example are to align with respective apertures or bores of the yoke 106. The fasteners 120 (FIG. 1) are to extend through the respective apertures 206 of the bracket 116 and be received by the apertures or bores of the yoke 106. In some examples, the fasteners 120 are threaded and received by respective threaded apertures or bores of the yoke 106. To ensure that the bracket 116 is rigidly fixed, coupled and/or fastened to the actuator 102, the threaded fasteners 120 are rotated until the coupling 122 (FIG. 1) of the bracket 116 and the actuator 102 is secure.

As illustrated in FIG. 2, the first side 204 of the bracket 116 defines ribs 210 to increase a rigidity of the bracket 116. In the illustrated example, an outer edge 212 of each of the ribs 210 forms an outer surface 214 of the first side 204 of the bracket 116. A recessed surface 216 of the first side 204 is spaced apart from the outer surface 214 in a direction toward the second side 302. As illustrated in FIG. 2, the ribs 210 intersect to form a web-like pattern such that the ribs 210 and the recessed surface 216 define cavities 218. In some example, the ribs 210 form polygonal profiles of the respective cavities 218. For example, some of the cavities 218 of FIG. 2 have triangular shapes or profiles.

The bracket assembly 100 of the illustrated example includes a sensor 220 that is coupled to the first side 204 of the bracket 116. As illustrated in FIG. 2, the sensor 220 is fixed to the recessed surface 216 within a cavity 222 (e.g., one of the cavities 218) adjacent the first end 118 of the bracket 116. The sensor 220 is coupled to the recessed surface 216 via, for example, an adhesive, potting material and/or a mechanical fastener. In the illustrated example, the sensor 220 is disposed within the cavity 222 to protect the sensor 220 from being damaged and/or dislodged by other objects (e.g., the actuator 102). The sensor 220 is fixed between the apertures 206 to enable the sensor 220 to measure a characteristic of the coupling 122 of the bracket 116 and the actuator 102.

As illustrated in FIG. 2, the sensor 220 is coupled to a first end 224 of a cable or wire 226 that communicatively couples the sensor 220 and the controller 114 (FIG. 1). The wire 226 enables the sensor 220 to communicate the measured characteristics of the first end 118 of the bracket 116 to the controller 114. In some examples, the wire 226 includes an electrically-insulating coating or jacket to prevent the wire 226 from shorting to the bracket 116 and/or any other object. In the illustrated example, a second end 228 of the wire 226 opposite the first end 224 extends through an opening 230 defined by the bracket 116. The opening 230 enables the second end 228 of the wire 226 to couple to the controller 114. As illustrated in FIG. 2, the opening 230 extends between the recessed surface 216 of the first side 204 and the second side 302 of the bracket 116.

In the illustrated example, at least one of the ribs 210 defined by the first side 204 is positioned between the sensor 220 and the opening 230. As illustrated in FIG. 2, each of the ribs 210 positioned between the sensor 220 and the opening 230 define a groove 232 that receives the wire 226. For example, the wire 226 is fixedly received by the grooves 232 via potting material, an adhesive and/or a mechanical fastener. In other examples, the ribs 210 define apertures spaced apart from the outer edge 212 of the ribs 210 through which the wire 226 extends from the sensor 220 to the opening.

In some examples, the grooves 232 enable the wire 226 to be recessed from the outer edge 212 of the ribs 210. As a result, the grooves 232 substantially reduce the risk of the wire 226 being damaged by the actuator 102 and/or any other object. For example, the grooves 232 prevent the wire 226 from being pinched, severed and/or otherwise damaged by the actuator 102 when the bracket 116 is coupled to the actuator 102.

Figure 3:
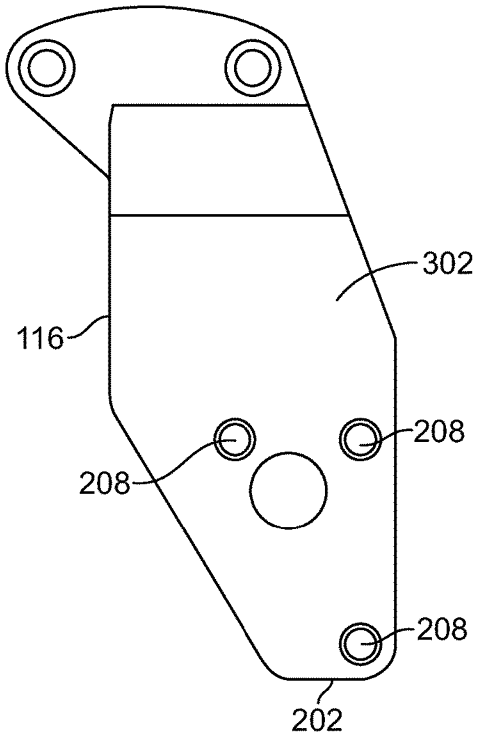
FIG. 3 depicts a second side of the bracket of FIG. 2.

FIG. 3 depicts the second side 302 of the bracket 116 that is opposite the first side 204 shown in FIG. 2. The apertures 208 defined at the second end 202 of the illustrated example enable the controller 114 (FIG. 1) to couple to the second side 302 at the second end 202 of the bracket 116. The apertures 208 at the second end 202 are to align with respective apertures or bores of the controller 114. To securely and/or rigidly couple the controller 114 to the bracket 116, fasteners (e.g., fasteners 402 of FIG. 4) extend through the respective apertures 208 of the bracket 116 and are received by the respective apertures or bores of the controller 114. In some examples, the fasteners 402 are threaded and are received by respective threaded apertures or bores of the controller 114.

Figure 4:
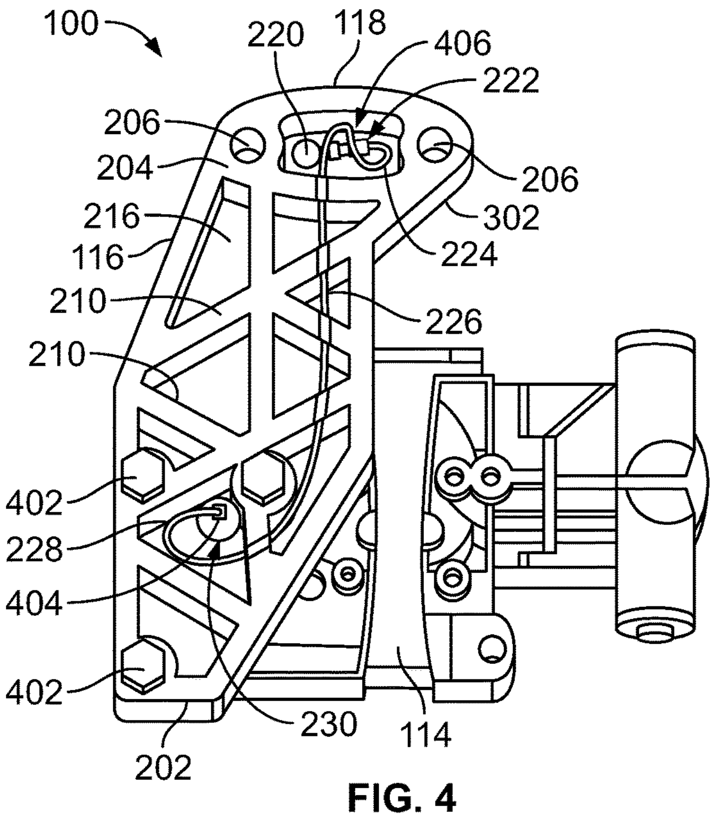
FIG. 4 depicts the example bracket assembly of FIG. 1 having the bracket of FIGS. 2-3 and a sensor.

FIG. 4 depicts the example bracket assembly 100 coupled to the controller 114. In the illustrated example, the controller 114 is coupled to the second side 302 of the bracket 116 via the fasteners 402 (e.g., threaded fasteners) that extend through the apertures 208 (FIG. 2) of the bracket 116. Thus, as illustrated in FIG. 4, the controller 114 is coupled to the second side 302 at the second end 202 of the bracket 116.

In the illustrated example, the sensor 220 is coupled to first side 204 at the first end 118 of the bracket 116 and is communicatively coupled to the controller 114 via the wire 226. The first end 224 of the wire 226 is coupled to the sensor 220, and the second end 228 of the wire 226 is coupled to the controller 114 via a terminal or receptacle 404 of the controller 114. As illustrated in FIG. 4, the second end 228 of the wire 226 extends through the opening 230 of the bracket 116 and is received by the receptacle 404 adjacent the opening 230. In some examples, the opening 230 is defined by the bracket 116 such that the opening 230 aligns with the receptacle 404 when the controller 114 is coupled to the bracket 116.

As illustrated in FIG. 4, the sensor 220 is disposed in the cavity 222 between the apertures 206 that enable the bracket 116 to couple to the actuator 102 (FIG. 1). When the bracket 116 of the illustrated example is coupled to a surface of the actuator 102, the sensor 220 is enclosed by the recessed surface 216, the adjacent ribs 210, and the surface of the actuator 102. As a result, the sensor 220 is protected from being dislodged and/or damaged by the actuator 102 and/or any other object when the bracket 116 is coupled to the actuator 102.

The sensor 220 of the illustrated example measures a characteristic of a portion 406 of the bracket 116 immediately adjacent the coupling 122 (FIG. 1) of the bracket 116 and the actuator 102. Because the portion 406 is immediately adjacent the coupling 122, the characteristics of the portion 406 measured by the sensor 220 are substantially similar (e.g., identical) to the characteristics of the coupling 122. As a result, the sensor 220 is able to accurately measure a characteristic of the coupling 122 when the sensor 220 is coupled to the first end 118 of the bracket 116. Thus, the sensor 220 is capable of accurately measuring a characteristic (e.g., a force, a strain, an acceleration, an acoustic emission) that indicates whether the coupling 122 of the bracket 116 and the actuator 102 is secure and/or rigid. Otherwise, if the sensor 220 is substantially spaced apart from the coupling 122, the measurements of the sensor 220 may not accurately reflect a characteristic of the coupling 122. In some example, the characteristic measured by the sensor 220 is further indicative of whether the yoke 106 of the actuator 102 is cracked, the yoke lock nut 107 is loosened, the tubing 110 has failed and/or the controller 114 is securely coupled to the bracket 116.

The sensor 220 of the illustrated example is an accelerometer. In some examples, the sensor 220 is a single-axis accelerometer or a tri-axial accelerometer. A single-axis accelerometer measures a proper acceleration (e.g., g-force) of an object (e.g., the first end 118 of the bracket 116) in one direction, and a tri-axial accelerometer measures a proper acceleration of an object in three perpendicular directions. For example, accelerometers are used to measure accelerations of vibrations of machinery (e.g., the actuator 102). The measured accelerations of vibrations are used to calculate an acceleration spectral density to detect degradation and/or failure initiation of the rotary machinery. Acceleration spectral density is a calculation of the square of the average amplitude of a vibration at a vibration frequency bandwidth (e.g., square of the root mean square g-level of a signal over a frequency bandwidth ($grms^2/Hz$)).

In the illustrated example, the acceleration spectral density is calculated based on the accelerations of vibrations measured by the sensor 220 of the portion 406 at the first end 118 of the bracket 116. Because the portion 406 is immediately adjacent the coupling 122, the controller 114 analyzes the calculated acceleration spectral density (e.g., via Fourier transform analysis, Cepstrum analysis, skewness and kurtosis analysis, phase and modal analysis, etc.) to determine whether the bracket 116 is securely and/or rigidly fixed, fastened and/or coupled to the actuator 102. For example, when the fasteners 120 (FIG. 1) that couple the first end 118 of the bracket 116 to the yoke 106 (FIG. 1) are loose, the controller 114 identifies a shift in a resonant frequency (e.g., a positive or negative shift) and/or a change in a frequency amplitude (e.g., a dampening or amplification) of the calculated acceleration spectral density that is indicative of a loose coupling. In some examples, a shift in a resonant frequency and/or a change in a frequency amplitude of the calculated acceleration spectral density is indicative of the yoke 106 cracking, the yoke lock nut 107 loosening, the tubing 110 failing and/or the controller 114 decoupling from the bracket 116.

While the sensor 220 of the illustrated example is an accelerometer, other types of sensors may be used to identify a characteristic of the bracket 116 and/or the actuator 102. In some examples, the sensor 220 is a force gauge that measures a force imparted to the portion 406 of the bracket 116. In some examples, the sensor 220 is a strain gauge that measures a strain of the portion 406 of the bracket 116. In some examples, the sensor 220 is an acoustic emission sensor that measures acoustic emissions of the first end 118 of the bracket 116 to determine if the bracket 116 and/or the actuator 102 are physically altered. For example, the acoustic emission sensor can identify whether the bracket 116 has been physically altered in such a manner that compromises the coupling 122 of the bracket 116 and the actuator 102 (e.g., a crack has formed along one of the apertures 206).

Figure 5:
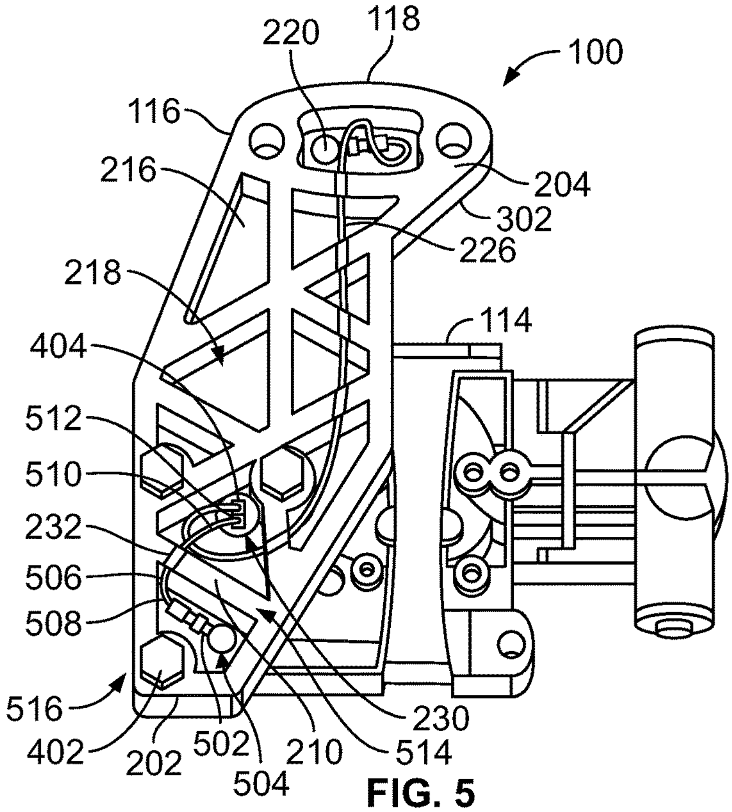
FIG. 5 depicts the example bracket assembly of FIG. 1 having the bracket of FIGS. 2-3 and two sensors.

FIG. 5 depicts the example bracket assembly 100 that includes the sensor 220 coupled to the first end 118 of the bracket 116 and a sensor 502 coupled to the second end 202. As illustrated in FIG. 5, the controller 114 is coupled to the second side 302 at the second end 202 of the bracket 116 via the fasteners 402, and the sensor 220 is coupled to the first side 204 at the first end 118 of the bracket 116. The wire 226 is coupled to the sensor 220 and is received by the receptacle 404 of the controller 114 to communicatively couple the sensor 220 and the controller 114.

In the illustrated example, the sensor 502 is coupled to the recessed surface 216 of the first side 204 at the second end 202 of the bracket 116. The sensor 502 is disposed within a cavity 504 (e.g., one of the cavities 218) at the second end 202 of the bracket 116 to protect the sensor 502 from being damaged and/or dislodged. The sensor 502 is coupled to the bracket 116 via, for example, an adhesive, potting material and/or a mechanical fastener.

As illustrated in FIG. 5, the sensor 502 is communicatively coupled to the controller 114 via a cable or wire 506. A first end 508 of the wire 506 is coupled to the sensor 502. A second end 510 of the wire 506 opposite the first end 508 extends through the opening 230 of the bracket 116 and is received by a receptacle 512 of the controller 114. As illustrated in FIG. 5, each of the ribs 210 positioned between the sensor 502 and the opening 230 defines one of the grooves 232 that substantially reduce the risk of the wire 506 being pinched, severed and/or otherwise damaged.

To enable the measurement of the sensor 502 to be compared to the measurement of the sensor 220, each of the sensors 220, 502 of the illustrated example of FIG. 5 is an accelerometer. For example, the sensor 220 measures the acceleration at the first end 118 of the bracket 116, and the sensor 502 measures the acceleration at the opposing second end 202. Based on the measured accelerations, the controller 114 calculates an acceleration spectral density associated with the bracket 116. In other examples, both of the sensors 220, 502 are a force gauge, a strain gauge, an acoustic emission sensor, or another type of sensor that enable the measurement of the sensor 502 to be compared to the measurement of the sensor 220.

Because the bracket 116 of illustrated example is coupled to the actuator 102 only at the first end 118, the second end 202 of the bracket 116 is unsupported. As a result, vibrational energy of the bracket 116 is transmitted across the bracket 116 (e.g., from the first end 118 to the second end 202). In some examples, the acceleration spectral density calculated from the acceleration measurements of the sensors 220, 502 indicates a vibrational energy characteristic of the bracket 116. For example, the controller 114 analyzes the acceleration spectral density (e.g., via Fourier transform analysis, Cepstrum analysis, skewness and kurtosis analysis, phase and modal analysis, etc.) to calculate or determine a transmissibility of the bracket 116 that represents a ratio of vibrational energy transmitted through the bracket 116. Thus, to determine the transmissibility of the bracket 116, measurements of the sensor 502, 220 are compared when the controller 114 is securely coupled to the second end 202 and the first end 118 is securely coupled to the actuator 102.

As illustrated in FIG. 5, the sensor 502 is coupled to the bracket 116 between the apertures 208 to enable the sensor 502 to measure a characteristic of a portion 514 of the second end 202 of the bracket 116. Because the portion 514 of the bracket 116 is immediately adjacent a coupling 516 of the bracket 116 and the controller 114, the characteristics of the portion 514 are substantially similar (e.g., identical) to the characteristics of the coupling 516. Further, the first sensor 220 measures a characteristic of the portion 406 of the first end 118 of the bracket 116. In some examples, a comparison of the measured characteristics of the sensors 220, 502 identifies degradation and/or damage of the actuator 102, the bracket 116, the coupling 122 of the bracket 116 and the actuator 102 and/or the coupling 516 of the controller 114 and the bracket 116.

For example, the sensors 220, 502 of the illustrated example enable the controller 114 to determine whether the controller 114 is securely and/or rigidly fixed, fastened and/or coupled to the second end 202 of the bracket 116. If a comparison of the measurements of the sensors 220, 502 corresponds to the transmissibility of the bracket 116, the controller 114 determines that the controller 114 is securely and/or rigidly coupled to the bracket 116. Conversely, the controller 114 determines that the controller 114 is unsecure and/or loosely coupled to the bracket 116 if a comparison of the measurements of the sensors 220, 502 identifies a shift in the resonant frequency and/or a change in the frequency amplitude that is indicative of a loose coupling. Thus, the sensors 220, 502 of the bracket assembly 100 enable the controller to determine whether the controller 114 is rigidly coupled to the bracket 116.

In some examples, a shift in the resonant frequency and/or a change in the frequency amplitude identified by a comparison of the measured characteristics of the sensors 220, 502 is further indicative of the yoke 106 cracking, the yoke lock nut 107 loosening, the tubing 110 failing and/or the coupling 122 between the bracket 116 and the actuator 102 loosening. For example, a shift in the resonant frequency and/or a change in the frequency amplitude by a first predetermined value is indicative of the coupling 516 of the controller 114 and the bracket 116 loosening, and a shift in the resonant frequency and/or a change in the frequency amplitude by a second predetermined value different than the first predetermined value is indicative of the yoke 106 cracking.

Figure 6:
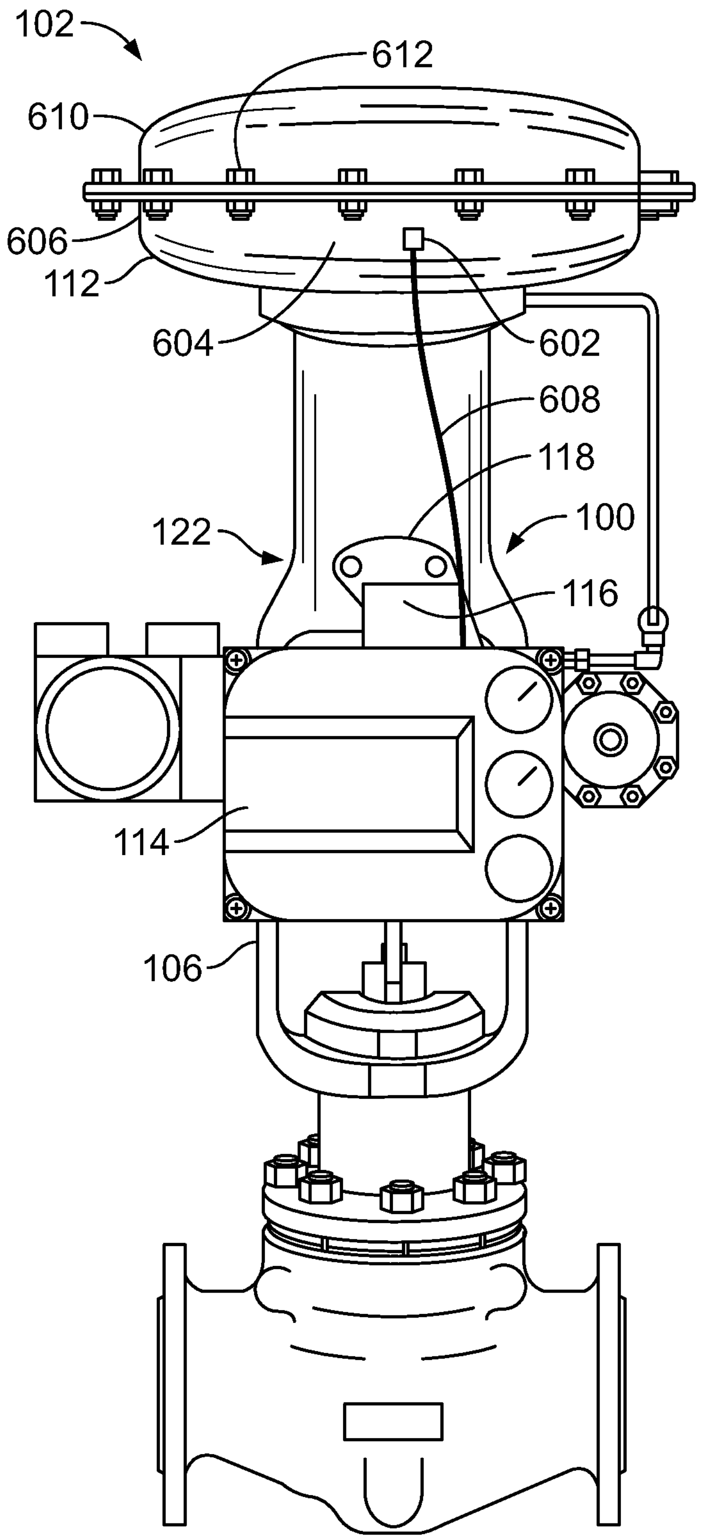
FIG. 6 depicts the example bracket assembly of FIG. 1 having a sensor coupled to the actuator.

FIG. 6 depicts the example bracket assembly 100 coupled to the yoke 106 of the actuator 102. In the illustrated example, the bracket assembly 100 includes the bracket 116, the sensor 220 (FIG. 2) coupled to the first end 118 of the bracket 116, and a sensor 602 coupled to the actuator 102. In the illustrated example, the sensor 602 is coupled to a surface 604 of a lower portion 606 of the actuator casing 112. A wire 608 is coupled between the sensor 602 and the controller 114 (e.g., via the receptacle 512 of FIG. 5) to communicatively couple the sensor 602 and the controller 114.

Each of the sensors 220, 602 of the illustrated example is an accelerometer that is communicatively coupled to the controller 114. As a result, the controller 114 is able to calculate an acceleration spectral density by comparing the acceleration measured at the surface 604 of the actuator casing 112 and the acceleration measured at the coupling 122 of the bracket 116 and the yoke 106. In other examples, both of the sensors 220, 602 are a force gauge, a strain gauge, an acoustic emission sensor, or another type of sensor to enable the measurements of the sensors 220, 602 to be compared by the controller 114.

In the illustrated example, the sensors 220, 602 enable the controller 114 to determine if a component of the actuator casing 112 (e.g., the lower portion 606 or an opposing upper portion 610 of the actuator casing 112) and/or another component (e.g., a diaphragm disposed within a cavity of the actuator casing 112) near the surface 604 of the actuator casing 112 is unsecure and/or loosely fixed. For example, a measurement of the sensor 220 is compared to a measurement of the sensor 602. The sensors 220, 602 identify degradation and/or decoupling of a component of the actuator casing 112 if there is a shift in a resonant frequency (e.g., a positive or negative shift) and/or a change in a frequency amplitude (e.g., a dampening or amplification) away from measurements of the sensors 220, 602 that are indicative of the actuator casing 112 being undamaged. In some examples, the calculated acceleration spectral density indicates a shift in the resonant frequency and/or a change in the frequency amplitude by a predetermined value that is associated with a loosening of bolts 612 that couple the lower and upper portions 606, 610 of the actuator casing 112. In such examples, the controller 114 communicatively coupled to the sensors 220, 602 determines that the bolts 612 have loosened from the lower portion 606 and/or the upper portion 610 of the actuator casing 112. Thus, the sensors 220, 602 of the bracket assembly 100 enable the controller 114 to determine whether components of the actuator 102 are securely fastened.

Figure 7A:
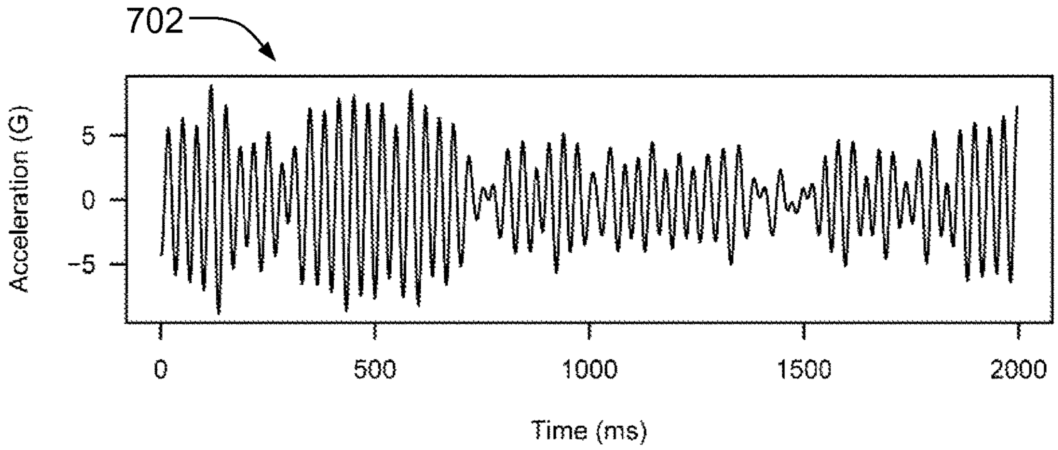
FIGS. 7A-7C depict example acceleration measurements of the example bracket assembly of FIG. 1.
Figure 7B:
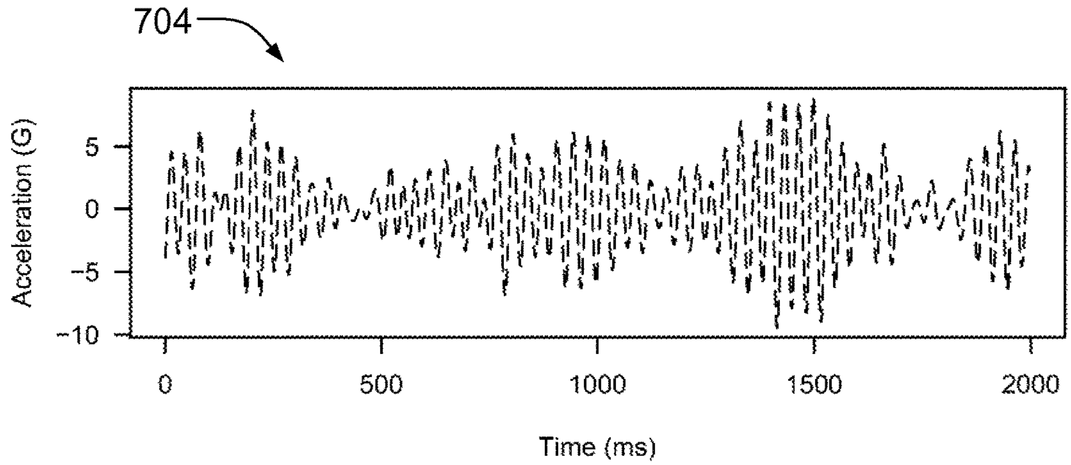
Figure 7C:
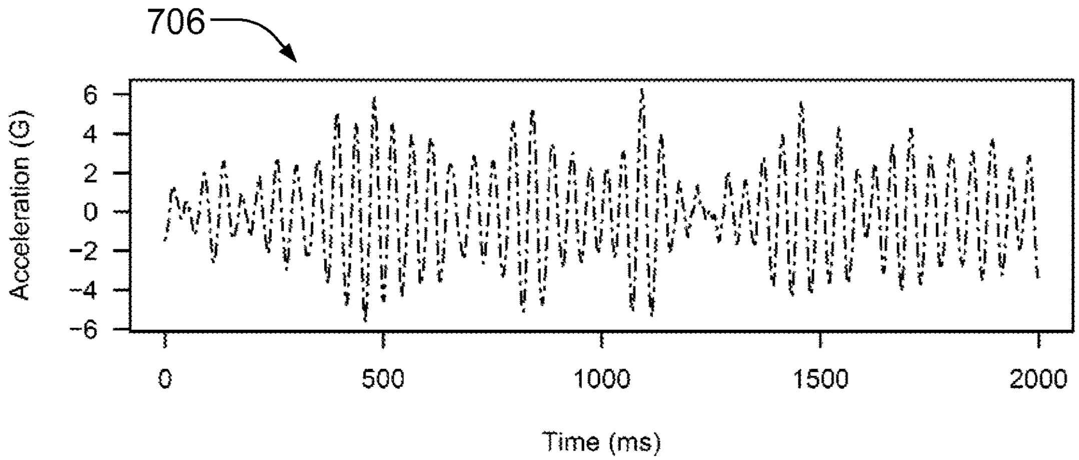

FIGS. 7A-7C depict example acceleration measurements of the bracket assembly 100 of FIG. 1. FIG. 7A depicts acceleration measurements 702 with a solid line, FIG. 7B depicts acceleration measurements 704 with a dashed line, and FIG. 7C depicts acceleration measurements 706 with a dotted line. In the illustrated examples, the acceleration measurements 702, 704, 706 are represented by g-force (G) of the acceleration over a period of time (e.g., 2 seconds). In some examples, the acceleration measurements 702, 704, 706 are obtained from the sensor 220 (FIG. 2) that is positioned at the first end 118 of the bracket 116 and the sensor 502 (FIG. 5) that is positioned at the second end 202 of the bracket 116.

In the illustrated examples, the acceleration measurements 702 of FIG. 7A are associated with a first period of time, the acceleration measurements 704 of FIG. 7B are associated with a subsequent second period of time, and the acceleration measurements 706 of FIG. 7C are associated with a subsequent third period of time. For example, the acceleration measurements 702 of FIG. 7A are obtained during a first day, the acceleration measurements 704 of FIG. 7B are obtained during a subsequent second day, and the acceleration measurements 706 of FIG. 7C are obtained during a subsequent third day.

Figure 8:
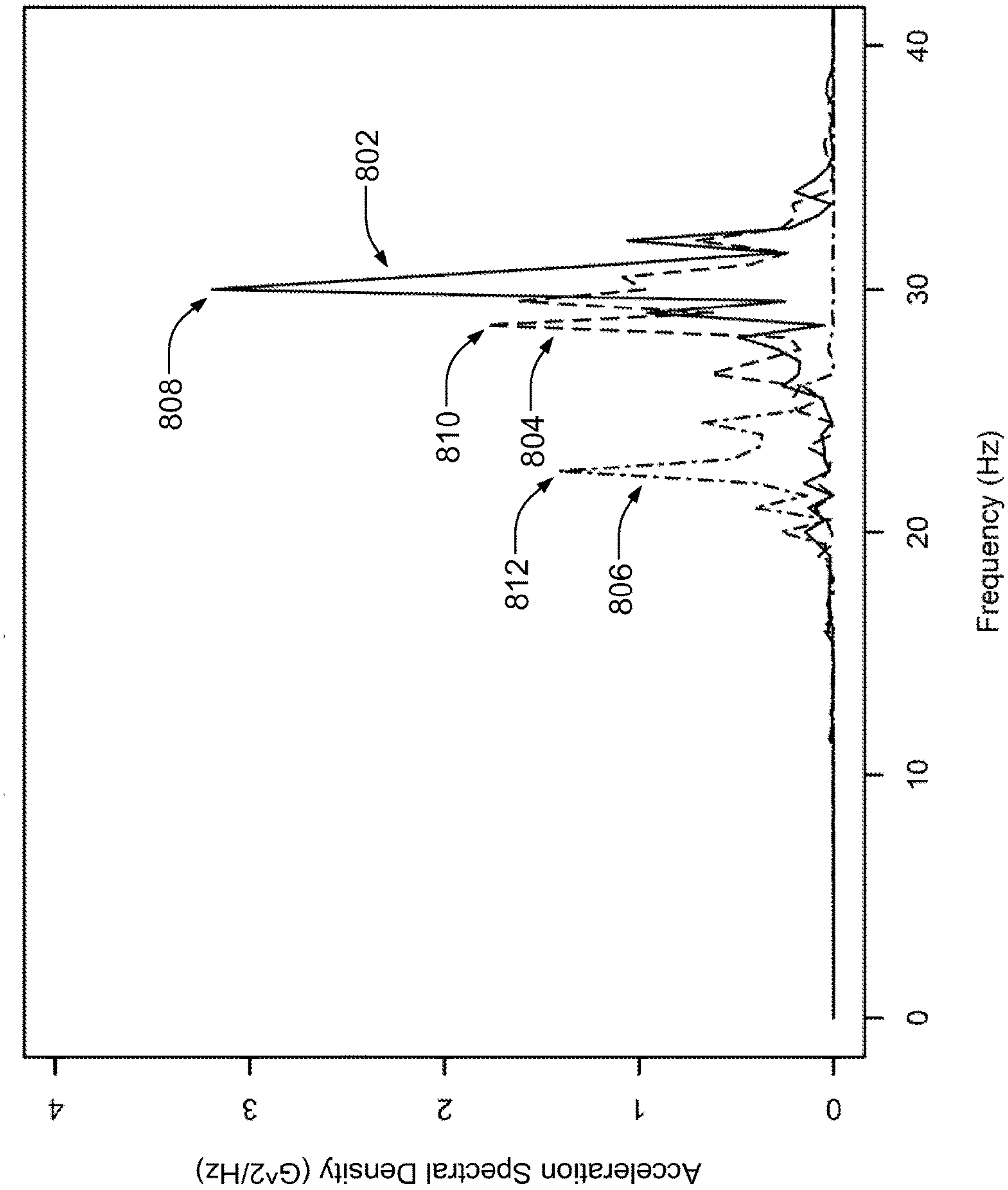
FIG. 8 depicts acceleration spectral densities associated with the acceleration measurements of FIGS. 7A-7C.

FIG. 8 depicts acceleration spectral densities 802, 804, 806 that are calculated based on the respective acceleration measurements 702, 704, 706 of FIGS. 7A-7C. The acceleration spectral densities 802, 804, 806 of the bracket 116 are shown over a range of frequencies (e.g., 0-40 Hz) in FIG. 8. In the illustrated example, the acceleration spectral density 802 associated with the first time period is represented with a solid line, the acceleration spectral density 804 associated with the second time period is represented with a dashed line, and the acceleration spectral density 806 associated with the third time period is represented with a dotted line.

As illustrated in FIG. 8, the acceleration spectral densities 802, 804, 806 indicate respective resonant frequencies 808, 810, 812 of the bracket 116. The resonant frequency 808 is associated with the first period of time, the resonant frequency 810 is associated with the second period of time, and the resonant frequency 812 is associated with the third period of time.

In the illustrated example, the resonant frequencies 808, 810, 812 of the bracket 116 indicate that the structural rigidity of the bracket 116 decreases (e.g., cracking growth of the bracket 116, loosening of the coupling 122 between the bracket 116 and the actuator 102, etc.) from the first period of time to the third period of time. In the illustrated example, the decrease in structural rigidity is identified by a negative shift of the resonant frequencies 808, 810, 812 over time. For example, a resonant frequency of the bracket 116 decreases from 30 Hz during the first period of time (e.g., the resonant frequency 808) to 28.5 Hz during the second period of time (e.g., the resonant frequency 810) to 22.5 Hz during the third period of time (e.g., the resonant frequency 812). Further, the resonant frequencies 808, 810, 812 of the illustrated example include additional and/or alternative indications of a decrease in structural rigidity. For example, the decrease in amplitudes of the respective resonant frequencies 808, 810, 812 over time and the increase in kurtosis of the respective resonant frequencies 808, 810, 812 (e.g., represented by a widening of the peaks of the resonant frequencies 808, 810, 812) represent an increase in vibrational energy over time and, thus, indicate a decrease in structural rigidity of the bracket 116 over time.

Figure 9:
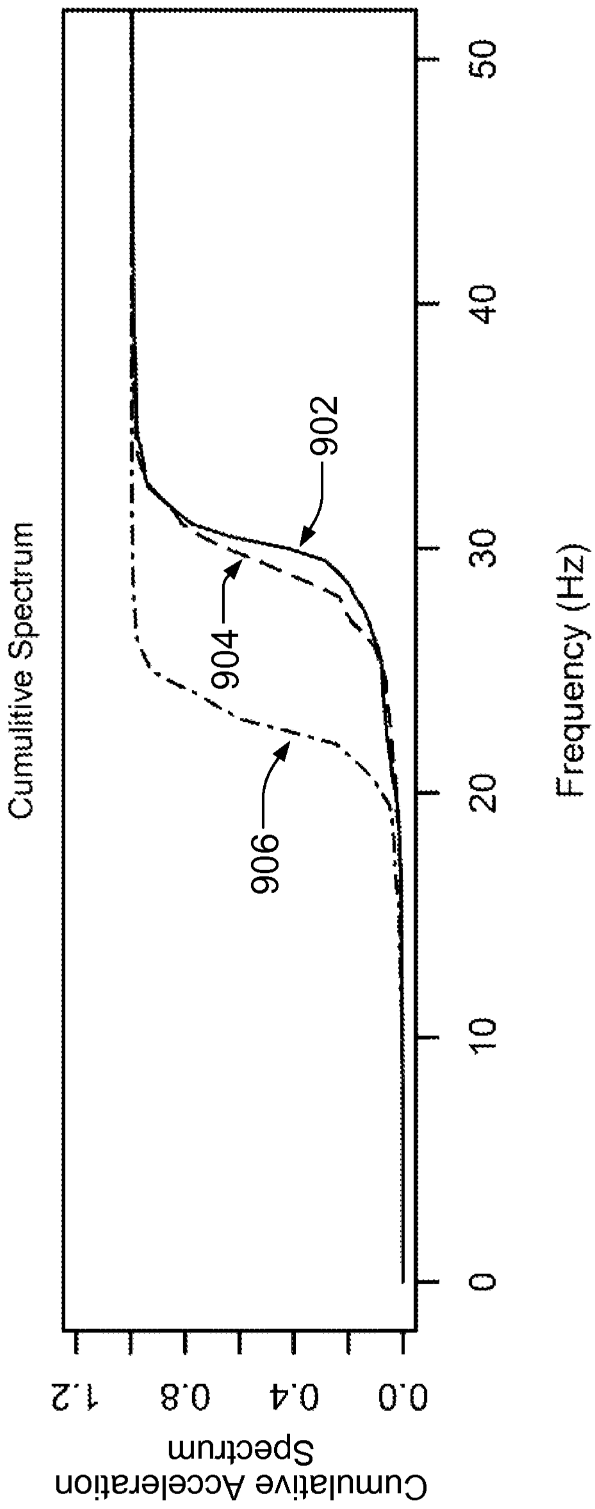
FIG. 9 depicts cumulative acceleration spectra associated with the acceleration spectral densities of FIG. 8.

FIG. 9 depicts cumulative acceleration spectra 902, 904, 906 associated with the acceleration spectral densities 802, 804, 806 of FIG. 8. The cumulative acceleration spectra 902, 904, 906 are shown in FIG. 9 over a range of frequencies (e.g., 0-40 Hz) until each of the cumulative acceleration spectra 902, 904, 906 is substantially equal to a value of 1.0. In the illustrated example, the cumulative acceleration spectrum 902 associated with the first time period is represented with a solid line, the acceleration spectral density 904 associated with the second time period is represented with a dashed line, and the acceleration spectral density 906 associated with the third time period is represented with a dotted line. In the illustrated example, a curve that reaches a cumulative acceleration spectrum of 1.0 at a lower frequency indicates decreased structural rigidity (e.g., as a result of crack growth, decoupling, etc.). Thus, the cumulative acceleration spectra 902, 904, 906 indicate that the structural rigidity of the bracket 116 decreases between the first period of time and the third period of time.

Although certain example apparatus have been described herein, the scope of coverage of this patent is not limited thereto. On the contrary, this patent covers all methods, apparatus and articles of manufacture fairly falling within the scope of the amended claims either literally or under doctrine of equivalents.

What is claimed is:

1. An apparatus comprising:

a bracket having a first side and a second side opposite the first side, the first side to directly couple to a first surface of an actuator, the second side to directly couple to a controller, wherein the first side of the bracket includes a plurality of cavities defined by a plurality of ribs, the ribs having a uniform height defining a plane of the first side; and a first sensor coupled to the first side of the bracket, wherein, when the bracket is coupled to the first surface of the actuator, the first sensor is adjacent the first surface to measure a characteristic of the first surface of the actuator, wherein the first sensor is disposed within one of the cavities between the plane of the first side and the second side.

2. The apparatus of claim 1, wherein the characteristic of the first surface of the actuator indicates a characteristic of at least one of a coupling of the bracket and the actuator, a coupling of a controller and the bracket, a yoke of the actuator, a yoke lock nut, and tubing between the controller and the actuator.

3. The apparatus of claim 1, wherein the first sensor is coupled to the bracket between at least two of the ribs and is recessed from an outer edge of the ribs to enclose the first sensor by the at least two of the ribs, the first side of the bracket, and the first surface of the actuator.

4. The apparatus of claim 3, wherein the first sensor is enclosed by the at least two ribs, the first side of the bracket, and the first surface of the actuator to prevent the first sensor from being damaged or dislodged.

5. The apparatus of claim 1, wherein an outer edge of at least one of the ribs defines a groove to fixedly receive a wire coupled to the first sensor via potting, the groove to prevent the wire from being damaged when the bracket is coupled to the actuator.

6. The apparatus of claim 5, wherein the wire is disposed between the plane and a surface of the groove of the rib.

7. The apparatus of claim 1, wherein the bracket defines an aperture that is to receive a wire extending between the first sensor and a receptacle of the controller to operatively couple the first sensor and the controller.

8. The apparatus of claim 1, wherein the first sensor is an acoustic emission sensor, a force gauge, or a strain gauge.

9. The apparatus of claim 1, further comprising a second sensor coupled to the first side of the bracket and spaced apart from the first sensor, wherein a characteristic measured by the second sensor and the characteristic measured by the first sensor are compared to identify a characteristic of at least one of a coupling of the bracket and the actuator, a coupling of a controller and the bracket, a yoke of the actuator, a yoke lock nut, and tubing between the controller and the actuator.

10. The apparatus of claim 1, further comprising a second sensor that is to couple to a second surface of the actuator different than the first surface, the second sensor to measure a characteristic of the second surface of the actuator.

11. The apparatus of claim 10, wherein, when the bracket is coupled to the controller and the actuator, the first sensor and the second sensor are operatively coupled to the controller to enable the characteristic of the coupling to be compared to the characteristic of the second surface.

12. The apparatus of claim 1, wherein the first sensor is an accelerometer to measure vibrations of the actuator to determine degradation of the actuator or a coupling of the bracket to the actuator.

13. The apparatus of claim 1, wherein the characteristic is indicative of a degree to which the bracket is rigidly coupled to the actuator.

14. The apparatus of claim 1, wherein the characteristic includes at least one of stress, strain, acceleration, vibration, and acoustic emissions.

15. The apparatus of claim 1, wherein the characteristic is indicative of a fatigue of one or more fasteners of the bracket.

16. The apparatus of claim 1, wherein the characteristic is indicative of a defect of the bracket.

17. The apparatus of claim 1, wherein the first sensor is positioned immediately adjacent a coupling of the bracket and the actuator to measure a characteristic of the coupling.

18. The apparatus of claim 1, wherein the first sensor is disposed between the plane and the second side to protect the sensor from damage.

19. An apparatus comprising:

means for coupling a controller to a surface of an actuator, wherein a first side of the means for coupling includes a plurality of cavities defined by a plurality of ribs, the ribs having a uniform height defining a plane of the first side; and means for sensing a characteristic coupled to the means for coupling, wherein, when the means for coupling is coupled to the actuator, the means for sensing is adjacent the surface to measure a characteristic of the means for coupling, wherein the means for sensing is disposed within one of the cavities between the plane of the first side and a second side of the means for coupling.

20. The apparatus of claim 19, wherein the means for coupling includes means for enabling a wire to extend between the means for sensing and the controller to operatively couple the means for sensing and the controller.

* * * * *